United States Patent

Müller et al.

Patent Number: 5,380,864
Date of Patent: Jan. 10, 1995

[54] HERBICIDAL HALOGENATED SULPHONYLAMINOCARBONYL-TRIAZOLINONES

[75] Inventors: Klaus-Helmut Müller, Duesseldorf; Peter Babczinski, Wuppertal; Hans-Joachim Santel, Leverkusen; Robert R. Schmidt, Bergisch Gladbach, all of Germany

[73] Assignee: Bayer Aktiengesellschaft, Leverkusen, Germany

[21] Appl. No.: 60,075

[22] Filed: May 10, 1993

Related U.S. Application Data

[60] Division of Ser. No. 859,216, Mar. 27, 1992, Pat. No. 5,238,910, which is a continuation-in-part of Ser. No. 580,900, Sep. 11, 1990, abandoned.

[30] Foreign Application Priority Data

Nov. 3, 1989 [DE] Germany .............................. 3936622

[51] Int. Cl.$^6$ .................. C07D 249/12; C07D 249/14
[52] U.S. Cl. ................................ 548/263.8; 548/263.6
[58] Field of Search ........................... 548/263.6, 263.8

[56] References Cited

PUBLICATIONS

Chem. Berichte vol. 102 (1969), pp. 755-766.

*Primary Examiner*—Patricia L. Morris
*Attorney, Agent, or Firm*—Sprung Horn Kramer & Woods

[57] ABSTRACT

Herbicidal halogenated sulphonylaminocarbonyl-triazolinones of the formula

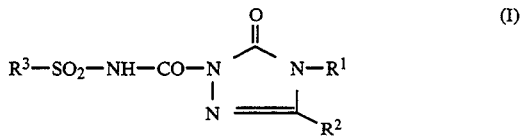

in which
  $R^1$ represents hydrogen, hydroxyl or amino, or represents an optionally substituted radical from the group consisting of alkyl, alkenyl, alkynyl, cycloalkyl, aralkyl, aryl, alkoxy, alkenyloxy, alkylamino, cycloalkylamino and dialkylamino,
  $R^2$ represents halogen and
  $R^3$ represents an optionally substituted radical from the group consisting of alkyl, aralkyl, aryl and heteroaryl,
and salts thereof.

6 Claims, No Drawings

HERBICIDAL HALOGENATED SULPHONYLAMINOCARBONYLTRIAZOLI- NONES

This is a division of application Ser. No. 07/859,216, filed Mar. 27, 1992, now U.S. Pat. No. 5,238,910, which is a continuation-in-part of application Ser. No. 07/580,900, filed Sep. 11, 1990, now abandoned.

The invention relates to new halogenated sulphonylaminocarbonyltriazolinones, to several processes for their preparation, and to their use as herbicides.

It is known that certain substituted aminocarbonylimidazolinones, such as, for example, 1-isobutylamino-carbonyl-2-imidazolidinone (isocarbamid), have herbicidal properties (cf. R. Wegler, Chemie der Pflanzenschutz- und Schädlingsbekäimpfungsmittel [Chemistry of Plant Protection Agents and Pesticides], Vol. 5, p. 219, Springer-Verlag, Berlin-Heidelberg-New York, 1977). However, the action of this compound is not satisfactory in all respects.

The new halogenated sulphonylaminocarbonyl-triazolinones of the general formula (I)

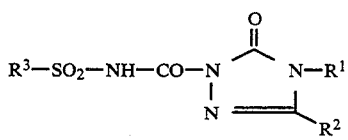

in which $R^1$ represents hydrogen, hydroxyl or amino, or represents an optionally substituted radical from the series comprising alkyl, alkenyl, alkynyl, cycloalkyl, aralkyl, aryl, alkoxy, alkenyloxy, alkylamino, cycloalkylamino and dialkylamino, $R^2$ represents halogen and $R^3$ represents an optionally substituted radical from the series comprising alkyl, aralkyl, aryl and heteroaryl, as well as salts of compounds of the formula (I) have now been found.

The new halogenated sulphonylaminocarbonyl-triazolinones of the general formula (I) are obtained when a) halogenated triazolinones of the general formula (II)

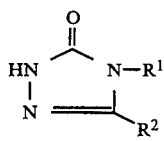

in which $R^1$ and $R^2$ have the abovementioned meanings, are reacted with sulphonyl isocyanates of the general formula (III)

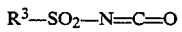

in which $R^3$ has the abovementioned meaning, if appropriate in the presence of a diluent, or when b) halogenated triazolinone derivatives of the general formula (IV)

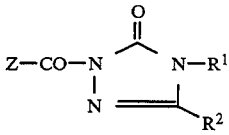

in which $R^1$ and $R^2$ have the abovementioned meanings and Z represents halogen, alkoxy, aralkoxy or aryloxy, are reacted with sulphonamides of the general formula (V)

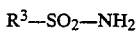

in which $R^3$ has the abovementioned meaning, if appropriate in the presence of an acid acceptor and if appropriate in the presence of a diluent, or when c) halogenated triazolinones of the general formula (II)

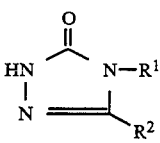

in which $R^1$ and $R^2$ have the abovementioned meanings, are reacted with sulphonamide derivatives of the general formula (VI)

in which $R^3$ has the abovementioned meaning and Z represents halogen, alkoxy, aralkoxy or aryloxy, if appropriate in the presence of an acid acceptor and if appropriate in the presence of a diluent, and, if desired, salts are formed by customary methods from the compounds of the formula (I) prepared by process (a), (b) or (c).

The new halogenated sulphonylaminocarbonyl-triazolinones of the general formula (I) and their salts are distinguished by a powerful herbicidal activity.

Surprisingly, the new compounds of the formula (I) have a considerably better herbicidal action than the known herbicide 1-isobutylaminocarbonyl-2-imidazol idinone (isocarbamid), which has a similar structure.

The invention preferably relates to compounds of the formula (I) in which $R^1$ represents hydrogen, hydroxyl or amino, or represents $C_1$-$C_6$-alkyl which is optionally substituted by fluorine, chlorine, bromine, cyano, $C_1$-$C_4$-alkoxy, $C_1$-$C_4$-alkylcarbonyl or $C_1$-$C_4$-alkoxy-carbonyl, or represents $C_3$-$C_6$-alkenyl or $C_3$-$C_6$-alkynyl, each of which is optionally substituted by fluorine, chlorine and/or bromine, or represents $C_3$-$C_6$-cycloalkyl which is optionally substituted by fluorine, chlorine, bromine and/or $C_1$-$C_4$-alkyl, or represents phenyl-$C_1$-$C_3$-alkyl which is optionally substituted by fluorine, chlorine, bromine, cyano, nitro, $C_1$-$C_4$-alkyl, trifluoromethyl, $C_1$-$C_4$-alkoxy and/or $C_1$-$C_4$-alkoxy-carbonyl, or represents phenyl which is optionally substituted by fluorine, chlorine, bromine, cyano, nitro, $C_1$-$C_4$-alkyl, trifluoromethyl, $C_1$-$C_4$-alkoxy, fluorine- and/or chlorine-substituted $C_1$-$C_3$-alkoxy, $C_1$-$C_4$-alkylthio, fluorine- and/or chlorine-substituted $C_1$-$C_3$-alkylthio, $C_1$-$C_4$-alkylsulphinyl, $C_1$-$C_4$-alkylsulphonyl and/or $C_1$-$C_4$-alkoxycarbonyl, or represents $CC_1$-$C_6$-alkoxy which is optionally substituted by fluorine, chlorine, cyano, $C_1$-$C_4$- alkoxy or $C_1$–$C_4$-alkoxy-carbonyl, or represents $C_3$–$C_4$-alkenyloxy, or represents fluorine-, cyano-, phenyl-, $C_1$–$C_4$-alkoxy- or $C_1$–$C_4$-alkoxy-carbonyl-substituted $C_1$–$C_4$-alkylamino, $C_3$–$C_6$-cycloalkylamino, or represents di-($C_1$–$C_4$-alkyl)-amino, $R^2$ represents fluorine, chlorine, bromine or iodine and $R^3$ represents the group

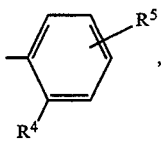

where $R^4$ and $R^5$ are identical or different and represent hydrogen, fluorine, chlorine, bromine, iodine, nitro, $C_1$–$C_6$-alkyl (which is optionally substituted by fluorine, chlorine, bromine, cyano, carboxyl, $C_1$–$C_4$-alkoxycarbonyl, $C_1$–$C_4$-alkylamino-carbonyl, di-($C_1$–$C_4$-alkyl)amino-carbonyl, hydroxyl, $C_1$–$C_4$-alkoxy, formyloxy, $C_1$–$C_4$-alkylcarbonyloxy, $C_1$–$C_4$-alkoxy-carbonyloxy, $C_1$–$C_4$-alkylamino-carbonyloxy, $C_1$–$C_4$-alkylthio, $C_1$–$C_4$-alkylsulphinyl, $C_1$–$C_4$-alkylsulphonyl, di-($C_1$–$C_4$-alkyl)-aminosulphonyl, $C_3$–$C_6$-cycloalkyl or phenyl), or represent $C_2$–$C_6$-alkenyl (which is optionally substituted by fluorine, chlorine, bromine, cyano, $C_1$–$C_4$-alkoxy-carbonyl, carboxyl or phenyl), or represent $C_2$–$C_6$-alkynyl (which is optionally substituted by fluorine, chlorine, bromine, cyano, $C_1$–$C_4$-alkoxy-carbonyl, carboxyl or phenyl), or represent $C_1$–$C_4$-alkoxy (which is optionally substituted by fluorine, chlorine, bromine, cyano, carboxyl, $C_1$–$C_4$-alkoxy-carbonyl, $C_1$–$C_4$-alkoxy, $C_1$–$C_4$-alkylthio, $C_1$–$C_4$-alkylsulphinyl or $C_1$–$C_4$-alkylsulphonyl), or represent $C_1$–$C_4$-alkylthio (which is optionally substituted by fluorine, chlorine, bromine, cyano, carboxyl, $C_1$–$C_4$-alkoxy-carbonyl, $C_1$–$C_4$-alkylthio, $C_1$–$C_4$-alkylsulphinyl or $C_1$–$C_4$-alkylsulphonyl), or represent $C_3$–$C_6$-alkenyloxy (which is optionally substituted by fluorine, chlorine, bromine, cyano or $C_1$–$C_4$-alkoxy-carbonyl), or represent $C_2$–$C_6$-alkenylthio (which is optionally substituted by fluorine, chlorine, bromine, cyano, nitro, $C_1$–$C_3$-alkylthio or $C_1$–$C_4$-alkoxycarbonyl), $C_3$–$C_6$-alkinyloxy, $C_3$–$C_6$-alkinylthio or the radical —S(O)$_p$—$R^6$, where p represents the numbers 1 or 2 and $R^6$ represents $C_1$–$C_4$-alkyl (which is optionally substituted by fluorine, chlorine, bromine, cyano or $C_1$–$C_4$-alkoxy-carbonyl), $C_3$–$C_6$-alkenyl, $C_3$–$C_6$-alkynyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)-amino and phenyl, or represents the radical —NHOR$^7$, where $R^7$ represents $C_1$–$C_{12}$-alkyl (which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylcarbonyl, $C_1$–$C_4$-alkoxycarbonyl, $C_1$–$C_4$-alkylaminocarbonyl or di-($C_1$–$C_4$-alkyl)-amino-carbonyl), or represents $C_3$–$C_6$-alkenyl (which is optionally substituted by fluorine, chlorine or bromine), $C_3$–$C_6$-alkinyl, $C_3$–$C_6$-cycloalkyl, $C_3$–$C_6$-cycloalkyl-$C_1$–$C_2$-alkyl, phenyl-$C_1$–$C_2$-alkyl (which is optionally substituted by fluorine, chlorine, nitro, cyano, $C_1$–$C_4$-alkyl, $C_1$–$C_4$-alkoxy or $C_1$–$C_4$-alkoxycarbonyl), or represents benzhydryl, or represents phenyl (which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxycarbonyl), $R^4$ and/or $R^5$ furthermore represent phenyl or phenoxy, or represent $C_1$–$C_4$-alkylcarbonylamino, $C_1$–$C_4$-alkoxy-carbonylamino, $C_1$–$C_4$-alkylamino-carbonylamino and di-($C_1$–$C_4$-alkyl)-amino-carbonylamino or represent the radical —CO—$R^8$, where $R^8$ represents $C_1$–$C_6$-alkyl, $C_1$–$C_6$-alkoxy, $C_3$–$C_6$-cycloalkoxy, $C_3$–$C_6$-alkenyloxy, $C_1$–$C_4$-alkylthio, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino (which are optionally substituted by fluorine and/or chlorine), $R^4$ and/or $R^5$ furthermore represent trimethylsilyl, thiazolinyl, $C_1$–$C_4$-alkylsulphonyloxy or di-($C_1$–$C_4$-alkyl)-aminosulphonylamino or represent the radical —CH=N—$R^8$, where $R^9$ is $C_1$–$C_6$-alkyl which is optionally substituted by fluorine, chlorine, cyano, carboxyl, $C_1$–$C_4$-alkoxy, $C_1$–$C_4$-alkylthio, $C_1$–$C_4$-alkylsulphinyl or $C_1$–$C_4$-alkylsulphonyl, or represents benzyl which is optionally substituted by fluorine or chlorine, or represents $C_3$–$C_6$-alkenyl or $C_3$–$C_6$-alkynyl, each of which is optionally substituted by fluorine or chlorine, or represents phenyl which is optionally substituted by fluorine, chlorine, bromine, $C_1$–$C_4$-alkyl, $C_1$–$C_4$-alkoxy, trifluoromethyl, trifluoromethoxy or trifluoromethylthio, or represent $C_1$–$C_6$-alkoxy, $C_3$–$C_6$-alkenoxy, $C_3$–$C_6$-alkynyloxy or benzyloxy, each of which is optionally substituted by fluorine and/or chlorine, or represents amino, $C_1$–$C_4$-alkylamino, di-($C_1$–$C_4$-alkyl)amino, phenylamino, $C_1$–$C_4$-alkyl-carbonylamino, $C_1$–$C_4$-alkoxycarbonyl-amino or $C_1$–$C_4$-alkyl-sulphonylamino, or represents phenylsulphonylamino which is optionally substituted by fluorine, chlorine, bromine or methyl, furthermore $R^3$ represents the radical

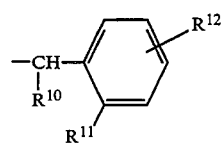

where $R^{10}$ represents hydrogen or $C_1$–$C_4$-alkyl, $R^{11}$ and $R^{12}$ are identical or different and represent hydrogen, fluorine, chlorine, bromine, nitro, cyano, $C_1$–$C_4$-alkyl (which is optionally substituted by fluorine and/or chlorine), $C_1$–$C_4$-alkoxy (which is optionally substituted by fluorine and/or chlorine ), carboxyl, $C_1$–$C_4$-alkoxy-carbonyl, dimethylaminocarbonyl, $C_1$–$C_4$-alkylsulphonyl or di-($C_1$–$C_4$-alkyl)-aminosulphonyl,; furthermore $R^3$ represents the radical

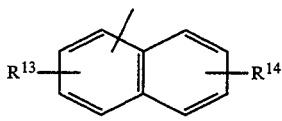

where $R^{13}$ and $R^{14}$ are identical or different and represent hydrogen, fluorine, chlorine, bromine, nitro, cyano, $C_1-C_4$-alkyl (which is optionally substituted by fluorine and/or chlorine) or $C_1-C_4$-alkoxy (which is optionally substituted by fluorine and/or chlorine); furthermore $R^3$ represents the radical

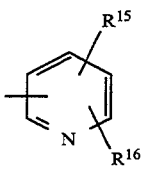

where $R^{15}$ and $R^{16}$ are identical or different and represent hydrogen, fluorine, chlorine, bromine, nitro, cyano, $C_1-C_4$-alkyl (which is optionally substituted by fluorine and/or chlorine), $C_1-C_4$-alkoxy (which is optionally substituted by fluorine and/or chlorine), or represent $C_1-C_4$-alkylthio, $C_1-C_4$-alkylsulphinyl or $C_1-C_4$-alkylsulphonyl (which are optionally substituted by fluorine and/or chlorine), or represent aminosulphonyl, mono-($C_1-C_4$-alkyl)-aminosulphonyl, di-($C_1-C_4$-alkyl)-aminosulphonyl or $C_1-C_4$-alkoxy-carbonyl or dimethylaminocarbonyl; furthermore $R^3$ represents the radical

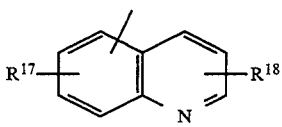

where $R^{17}$ and $R^{18}$ are identical or different and represent hydrogen, fluorine, chlorine, bromine, $C_1-C_4$-alkyl (which is optionally substituted by fluorine and/or bromine), $C_1-C_4$-alkoxy (which is optionally substituted by fluorine and/or chlorine), or represent $C_1-C_4$-alkylthio, $C_1-C_4$-alkylsulphinyl or $C_1-C_4$-alkylsulphonyl (which are optionally substituted by fluorine and/or chlorine), or represent di-($C_1-C_4$-alkyl)-aminosulphonyl; furthermore $R^3$ represents the radical

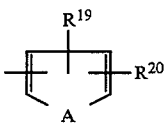

where $R^{19}$ and $R^{20}$ are identical or different and represent hydrogen, fluorine, chlorine, bromine, cyano, nitro, $C_1-C_4$-alkyl (which is optionally substituted by fluorine and/or chlorine), $C_1-C_4$-alkoxy (which is optionally substituted by fluorine and/or chlorine), $C_1-C_4$-alkylthio, $C_1-C_4$-alkylsulphinyl or $C_1-C_4$-alkylsulphonyl (which is optionally substituted by fluorine and/or chlorine), di-($C_1-C_4$-alkyl)-aminosulphonyl, $C_1-C_4$-alkoxy-carbonyl or dimethylaminocarbonyl, and A represents oxygen, sulphur or the group N-$Z^1$, where $Z^1$ represents hydrogen, $C_1-C_4$-alkyl (which is optionally substituted by fluorine, chlorine, bromine or cyano), $C_3-C_6$-cycloalkyl, benzyl, phenyl (which is optionally substituted by fluorine, chlorine, bromine or nitro ), $C_1-C_4$-alkylcarbonyl, $C_1-C_4$-alkoxy-carbonyl or di-($C_1-C_4$-alkyl)-aminocarbonyl; furthermore $R^3$ represents the radical

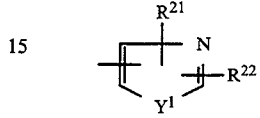

where $R^{21}$ and $R^{22}$ are identical or different and represent hydrogen, $C_1-C_4$-alkyl, halogen, $C_1-C_4$-alkoxycarbonyl, $C_1-C_4$-alkoxy or $C_1-C_4$-halogenoalkoxy, $Y^1$ represents sulphur or the group N-$R^{23}$, where $R^{23}$ represents hydrogen or $C_1-C_4$-alkyl; furthermore $R^3$ represents the radical

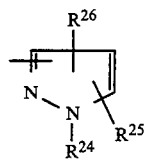

where $R^{24}$ represents hydrogen, $C_1-C_4$-alkyl, benzyl, pyridyl, quinolinyl or phenyl, $R^{25}$ represents hydrogen, halogen, cyano, nitro, $C_1-C_4$-alkyl (which is optionally substituted by fluorine and/or chlorine), $C_1-C_4$-alkoxy (which is optionally substituted by fluorine and/or chlorine), dioxolanyl or $C_1-C_4$-alkoxy-carbonyl and $R^{26}$ represents hydrogen, halogen or $C_1-C_4$-alkyl; furthermore $R^3$ represents one of the groups listed below:

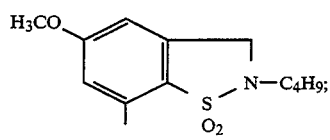

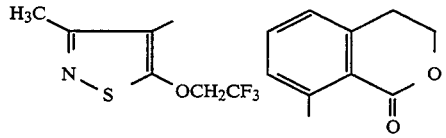

The invention also preferably relates to sodium salts, potassium salts, magnesium salts, calcium salts, ammonium salts, $C_1-C_4$-alkyl-ammonium salts, di-($C_1-C_4$-alkyl)-ammonium salts, tri-($C_1-C_4$-alkyl)-ammonium salts, $C_5$- or $C_6$-cycloalkyl-ammonium salts and di-($C_1-C_2$-alkyl)-benzyl-ammonium salts of compounds of the formula (I) in which $R^1$, $R^2$ and $R^3$ have the meanings indicated above as being preferred.

The invention particularly relates to compounds of the formula (I) in which $R^1$ represents hydrogen, or represents $C_1$-$C_4$-alkyl which is optionally substituted by fluorine, cyano, methoxy or ethoxy, or represents allyl, or represents $C_3$-$C_6$-cycloalkyl, or represents phenyl, or represents $C_1$-$C_4$-alkoxy, $C_3$-$C_4$-alkenyloxy, or represents $C_1$-$C_3$-alkylamino, $C_3$-$C_6$-cycloalkylamino, or represents di-($C_1$-$C_3$-alkyl)-amino, $R^2$ represents chlorine or bromine, and $R^3$ represents the group

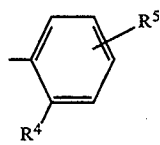

where $R^4$ represents fluorine, chlorine, bromine, methyl, trifluoromethyl, methoxy, difluoromethoxy, trifluoromethoxy, 2-chloro-ethoxy, 2-methoxyethoxy, $C_1$-$C_3$-alkylthio, $C_1$-$C_3$-alkylsulphinyl, $C_1$-$C_3$-alkylsulphonyl, dimethylaminosulphonyl, diethylaminosulphonyl, N-methoxy-N-methylaminosulphonyl, N-methoxyaminosulphonyl, phenyl, phenoxy or $C_1$-$C_3$-alkoxycarbonyl, and $R^5$ represents hydrogen, fluorine, chlorine or bromine; furthermore $R^3$ represents the radical

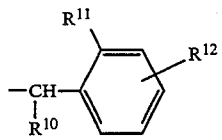

where $R^{10}$ represents hydrogen, $R^{11}$ represents fluorine, chlorine, bromine, methyl, methoxy, difluoromethoxy, trifluoromethoxy, ethoxy, methoxycarbonyl, ethoxycarbonyl, methylsulphonyl or dimethyalminosulphonyl, and $R^{12}$ represents hydrogen; furthermore $R^3$ represents the radical

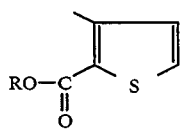

where R represents $C_1$-$C_4$-alkyl, or

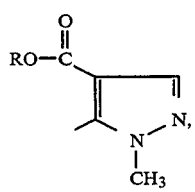

represents the radical where R represents $C_1$-$C_4$-alkyl.

Examples of the compounds according to the invention are listed in Table 1 below—cf. also the Preparation Examples.

TABLE 1

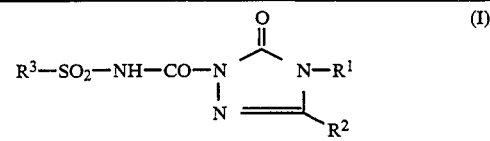

Examples of the compounds of the formula (I)

| $R^1$ | $R^2$ | $R^3$ |
|---|---|---|
| cyclopropyl | Br | 2-F-phenyl |
| cyclopropyl | Cl | 2-Cl-phenyl |
| CH₃ | F | 2-COOCH₃-phenyl |
| CH₃ | Cl | 2-OCHF₂-phenyl |
| CH₃ | Br | 2-OCF₃-phenyl |
| C₂H₅ | F | 2-SCH₃-phenyl |
| CH₂—CH=CH₂ | Cl | 2-(O—CH₂—CH₂Cl)-phenyl |
| cyclopentyl | Cl | 2-COOC₂H₅-phenyl |
| cyclopropyl | Br | 3-methyl-2-COOCH₃-thienyl |
| cyclopropyl | Cl | 2-COOCH₃-benzyl |

TABLE 1-continued

Examples of the compounds of the formula (I)

$$R^3-SO_2-NH-CO-N-CO-N-R^1 \atop N=\!\!\!=\!\!\!<\!\!R^2 \quad (I)$$

| $R^1$ | $R^2$ | $R^3$ |
|---|---|---|
| CH₃ | Br | 2-(OCHF₂)-benzyl |
| CH₃ | Br | 2-(COOCH₃)-benzyl |
| C₂H₅ | Cl | 2-(OCF₃)-benzyl |
| OCH₃ | Cl | 2-(COOCH₃)-phenyl |
| O—CH₂—CH=CH₂ | Cl | 2-(SO₂CH₃)-phenyl |
| CH₃ | Cl | 2-F-phenyl |
| CH₃ | Br | 2-(SO₂—N(CH₃)₂)-phenyl |
| CH₃ | Cl | 2-(SO₂NHCOCH₃)-phenyl |
| C₂H₅ | Cl | 2-(COOC₂H₅)-5-(CHF₂O)-phenyl |
| C₃H₇ | Cl | 4-chloro-5-methyl-1-methyl-pyrazol-3-yl |
| cyclopropyl | Cl | 1-(isoquinolin-1-yl)-3-methyl-4-(COOCH₃)-pyrazol-5-yl |
| CH₃ | Cl | 1-methyl-3-methyl-4-(COOC₂H₅)-pyrazol-5-yl |
| N(CH₃)₂ | Cl | 3-methyl-2-(COOCH₃)-thien-2-yl |
| N(CH₃)₂ | F | 3-(CF₃)-2-methyl-pyridin-yl |
| CH₃ | Cl | 2-methyl-3-(CON(CH₃)₂)-pyridin-yl |
| CH₃ | Cl | 2-methyl-3-(SO₂NH₂)-pyridin-yl |
| C₂H₅ | Cl | 2,6-dimethyl-3-(CON(CH₃)₂)-pyridin-yl |
| cyclopropyl | Br | 2-(OCH₂—CH₂—OCH₃)-phenyl |
| cyclopropyl | Cl | 2-(O—CH₂—CH₂—Cl)-phenyl |

TABLE 1-continued
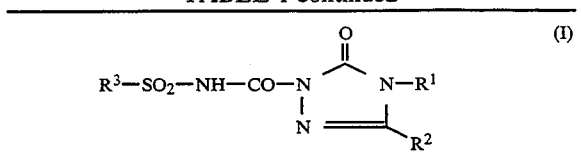
Examples of the compounds of the formula (I)
TABLE 1-continued
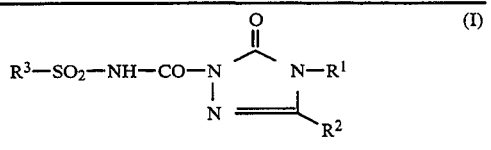
Examples of the compounds of the formula (I)

TABLE 1-continued

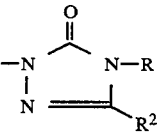

Examples of the compounds of the formula (I)

| R¹ | R² | R³ |
|---|---|---|
| CH₂—CHBr—CH₂—Br | Br | 2-(OCHF₂)-phenyl-CH₂— |
| CH₃ | Cl | 2-(SCH₃)-phenyl |
| CH₃ | Br | 2-(SO₂NCH₃(OCH₃))-phenyl |
| CH₃ | Cl | 2-(SO₂CH₃)-phenyl |
| CH₃ | F | 2-(NO₂)-phenyl |
| C₂H₅ | Cl | 2,6-(Cl)₂-phenyl-CH₂— |
| C₂H₅ | Br | 2,6-(OCHF₂)₂-phenyl |
| C₃H₇-n | Br | 2-(OCF₃)-phenyl |
| CH₃ | Cl | 2-(Cl)-phenyl |
| CH₃ | Br | 2-(SCH(CH₃)₂)-phenyl |

If, for example, 2,6-difluoro-phenylsulphonyl isocyanate and 5-bromo-4-ethyl-2,4-dihydro-3H-1,2,4-triazol-3-one are used as starting substances, the course of the reaction in process (a) according to the invention can be outlined by the following equation:

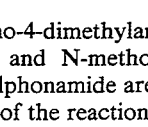

If, for example, 2-methoxy-benzenesulphonamide and 5-chloro-2-chlorocarbonyl-4-methoxy-2,4-dihydro-3H-1,2,4-triazol-3-one are used as starting substances, the course of the reaction in process (b) according to the invention can be outlined by the following equation:

If, for example, 5-bromo-4-dimethylamino-2,4-dihydro-3H-1,2,4-triazol-3-one and N-methoxycarbonyl-2-trifluoromethyl-benzenesulphonamide are used as starting substances, the course of the reaction in process (c)

according to the invention can be outlined by the following equation:

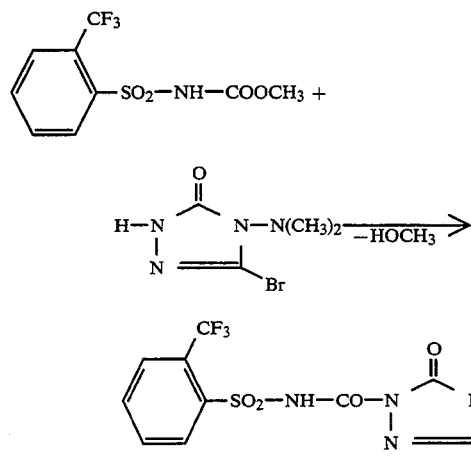

Formula (II) provides a general definition of the halogenated triazolinones to be used as starting substances in processes (a) and (c) according to the invention for the preparation of compounds of the formula (I).

In formula (II), $R^1$ and $R^2$ preferably, or in particular, have those meanings which have already been given above in connection with the description of the compounds of the formula (I) according to the invention as being preferred, or particularly preferred, for $R^1$ and Examples of the starting substances of the formula (II) are listed in Table 2 below.

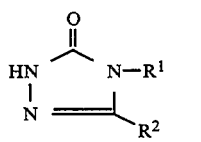
(II)

TABLE 2

| Examples of the starting substances of the formula (II): | |
|---|---|
| $R^1$ | $R^2$ |
| H | Br |
| $CH_3$ | Br |
| $C_2H_5$ | Br |
| $C_3H_7$ | Br |
| $CH(CH_3)_2$ | Cl |
| $C_4H_9$ | Cl |
| $CH_3$ | Cl |
| $C_2H_5$ | Cl |
| cyclopropyl | Br |
| $CH_2-CH=CH_2$ | Br |
| $CH(CH_3)_2$ | F |
| $CH_3$ | F |
| $C_3H_7$ | Cl |
| $C_2H_5$ | F |
| phenyl | Br |
| $N(CH_3)_2$ | Br |
| $N(CH_3)_2$ | Cl |
| $NH-CH_3$ | Br |

TABLE 2-continued

| Examples of the starting substances of the formula (II): | |
|---|---|
| $R^1$ | $R^2$ |
| $OCH_3$ | Br |
| $OCH_3$ | Cl |
| $C_2H_5$ | F |
| $C_3H_7$ | F |
| cyclopropyl | Cl |
| cyclopropyl | F |
| $OC_2H_5$ | Br |
| $OC_2H_5$ | Cl |
| $CH_2$-cyclopropyl | Br |
| $CH_2$-cyclopropyl | Cl |
| $C(CH_3)_3$ | Br |
| $CH_2-CH(CH_3)_2$ | Br |
| $CH_2-CH(CH_3)_2$ | Cl |
| $CH_2$-phenyl | Br |
| $O-C_3H_7$-n | Br |
| $CH_2$-(chlorocyclopropyl-Cl) | Br |
| $C_2H_5$ | I |
| $C_4H_9$ | Br |
| $CH(-C_2H_5)CH_3$ | Br |
| $CH(-C_2H_5)CH_3$ | Cl |
| $CH(CH_3)_2$ | Cl |
| $CH_2-CHBr-CH_2Br$ | Br |
| $CH_2-CHBr-CH_2Br$ | Cl |
| methylcyclopropyl | Br |
| methylcyclopropyl | Cl |
| cyclopentyl | F |
| cyclopentyl | Cl |

TABLE 2-continued

Examples of the starting substances of the formula (II):

| R¹ | R² |
|---|---|
| cyclopentyl | Br |
| cyclohexyl | Br |
| cyclohexyl | Cl |
| cyclobutyl | Br |
| cyclobutyl | Cl |
| OC₃H₇ | Cl |

The starting substances of the formula (II) are known and/or can be prepared by processes known per se (cf. Chem. Ber. 102 (1969), 755–766 and the Preparation Examples).

Formula (III) provides a general definition of the sulphonyl isocyanates also to be used as starting substances in process (a) according to the invention for the preparation of compounds of the formula (I).

In formula (III), $R^3$ preferably, or in particular, has the meaning which has already been mentioned above in connection with the description of the compounds of the formula (I) according to the invention as being preferred, or particularly preferred, for $R^3$.

The following may be mentioned as examples of the starting substances of the formula (III): 2-fluoro-, 2-chloro-, 2-bromo-, 2-methyl-, 2-methoxy-, 2-trifluoromethyl-, 2-difluoro-methoxy-, 2-trifluoromethoxy-, 2-methylthio-, 2-ethylthio-, 2-propylthio-, 2-methylsulphinyl-, 2-methylsulphonyl-, 2-dimethylaminosulphonyl-, 2-diethylaminosulphonyl-, 2-(N-methoxy-N-methyl)aminosulphonyl-, 2-phenyl-, 2-phenoxy-, 2-methoxycarbonyl-, 2-ethoxycarbonyl-, 2-propoxycarbonyl- and 2-isopropoxycarbonyl-phenylsulphonyl isocyanate, 2-fluoro-, 2-chloro-, 2-difluoromethoxy-, 2-trifluoromethoxy-, 2-methoxycarbonyl- and 2-ethoxycarbonyl-benzylsulphonyl isocyanate, 2-methoxycarbonyl-3-thienyl-sulphonyl isocyanate, 4-methoxycarbonyl- and 4-ethoxycarbonyl-1-methyl-pyrazol-5-yl-sulphonyl isocyanate.

The sulphonyl isocyanates of the formula (III) are known and/or can be prepared by processes known per se (cf. U.S. Pat. Nos. 4,127,405, 4,169,719, 4,371,391; EP-A 7,687, 13,480, 21,641, 23,141, 23,422, 30,139, 35,893, 44,808, 44,809, 48,143, 51,466, 64,322, 70,041, 173,312).

Process (a) according to the invention for the preparation of new compounds of the formula (I) is preferably carried out using diluents. Suitable diluents for this purpose are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

When carrying out process (a) according to the invention, the reaction temperatures can be varied within a substantial range. In general, the process is carried out at temperatures between 0° C. and 150° C., preferably at temperatures between 10° C. and 80° C.

Process (a) according to the invention is generally carried out under atmospheric pressure.

For carrying out process (a) according to the invention, between 1 and 3 moles, preferably between 1 and 2 moles, of sulphonyl isocyanate of the formula (III) are generally employed per mole of triazolinone of the formula (II).

The reactants can be combined in any desired sequence. The reaction mixture is stirred until the reaction is complete, concentrated, and the crude product which remains in the residue is crystallized using a suitable solvent, such as, for example, diethyl ether. The product of the formula (I) which is obtained as crystals is isolated by filtration with suction.

Formula (IV) provides a general definition of the triazolinone derivatives to be used as starting substances in process (b) according to the invention for the preparation of compounds of the formula (I).

In formula (IV), $R^1$ and $R^1$ preferably, or in particular, have those meanings which have already been mentioned above in connection with the description of the compounds of the formula (I) according to the invention as being preferred, or particularly preferred, for $R^1$ and $R^2$, and Z preferably represents chlorine, $C_1$-$C_4$-alkoxy, benzyloxy or phenoxy, in particular methoxy or phenoxy.

Examples which may be given for the starting substances of the formula (IV) are the compounds of the formula (IV) to be prepared from the compounds of the formula (II) listed in Table 2 and phosgene, methyl chloroformate, benzyl chloroformate, phenyl chloroformate or diphenyl carbonate.

The starting substances of the formula (IV) were hitherto unknown.

The new halogenated triazolinone derivatives of the formula (IV) are obtained when triazolinones of the general formula (II)

(II)

in which $R^1$ and $R^2$ have the abovementioned meanings, are reacted with carbonic acid derivatives of the general formula (XI)

$$Z\text{-CO-}Z^1 \qquad (XI)$$

in which Z has the abovementioned meaning and $Z^1$ represents a leaving group, such as chlorine, methoxy, benzyloxy or phenoxy, if appropriate in the presence of a diluent, such as, for example, tetrahydrofuran, and if appropriate in the presence of an acid acceptor, such as, for example, sodium hydride or potassium tert-butylate, at temperatures between $-20°$ C. and $+100°$ C. (cf. also the Preparation Examples).

Formula (V) provides a general definition of the sulphonamides also to be used as starting substances in process (b) according to the invention for the preparation of compounds of the formula (I).

In formula (V), $R^3$ preferably, or in particular, has the meaning which has already been mentioned above in connection with the description of the compounds of the formula (I) according to the invention as being preferred, or particularly preferred, for $R^3$.

The following may be mentioned as examples of the starting substances of the formula (V): 2-fluoro-, 2-chloro-, 2-bromo-, 2-methyl-, 2-methoxy-, 2-trifluoromethyl-, 2-difluoro-methoxy-, 2-trifluoromethoxy-, 2-methylthio-, 2-ethylthio-, 2-propylthio-, 2-methylsulphinyl-,2-methylsulphonyl-,2-dimethylaminosulphonyl-, 2-diethylaminosulphonyl-, 2-(N-methoxy-N-methyl)-aminosulphonyl-, 2-phenyl-, 2-phenoxy-, 2-methoxycarbonyl-, 2-ethoxycarbonyl-, 2-propoxycarbonyl- and 2 -isopropoxycarbonyl-benzenesulphonamide, 2-fluoro-, 2-chloro-, 2-difluoromethoxy-, 2-trifluoromethoxy-, 2-methoxycarbonyl- and 2-ethoxycarbonyl-phenylmethanesulphonamide, 2-methoxycarbonyl-3-thiophenesulphonamide, 4-methoxycarbonyl- and 4-ethoxycarbonyl-1-methylpyrazole-5-sulphonamide.

The sulphonamides of the formula (V) are known and/or can be prepared by processes known per se (cf. U.S. Pat. No. 4,127,405, 4,169,719, 4,371,391; EP-A 7,687, 13,480, 21,641, 23,141, 23,422, 30,139, 35,893, 44,808, 44,809, 48,143, 51,466, 64,322, 70,041, 173,312).

Process (b) according to the invention preparation of the new compounds of the formula (I) is preferably carried out using diluents. Suitable diluents for this purpose are virtually all inert organic solvents, for example those which are indicated above for process (a) according to the invention.

Acid acceptors which can be employed in process (b) according to the invention are all acid-binding agents which can customarily be employed for reactions of this type. The following are preferably suitable: alkali metal hydroxides, such as, for example, sodium hydroxide and potassium hydroxide, alkaline earth metal hydroxides, such as, for example, calcium hydroxide, alkali metal carbonates and alkali metal alcoholates, such as sodium carbonate, potassium carbonate, sodium tert-butylate and potassium tert-butylate, furthermore aliphatic, aromatic or heterocyclic amines, for example triethylamine, trimethylamine, dimethylaniline, dimethylbenzylamine, pyridine, 1,5-diazabicyclo-[4.3.0]-non-5-ene (DBN), 1,8 -diazabicyclo-[5.4.0]-undec-7-ene (DBU) and 1,4-diazabicyclo-[2.2.2]-octane (DABCO).

When carrying out process (b) according to the invention, the reaction temperatures can be varied within a substantial range. In general, the process is carried out at temperatures between 0° C. and 100° C., preferably at temperatures between 10° C. and 60° C.

Process (b) according to the invention is generally carried out under atmospheric pressure. However, it is also possible to carry out the process under increased or reduced pressure.

For carrying out process (b) according to the invention, the specifically required starting substances are generally employed in approximately equimolar amounts. However, it is also possible to use one of the two specifically employed components in a substantial excess. The reactions are generally carried out in a suitable diluent in the presence of an acid acceptor, and the reaction mixture is stirred for several hours at the specifically required temperature. Working-up in process (b) according to the invention is carried out in each case by customary methods.

The halogenated triazolinones of the formula (II) to be used as starting substances in process (c) according to the invention for the preparation of compounds of the formula (I) have already been described as starting substances for process (a) according to the invention.

Formula (VI) provides a general definition of the sulphonamide derivatives also to be used as starting substances in process (c) according to the invention for the preparation of compounds of the formula (I).

In formula (VI), $R^3$ and Z preferably, or in particular, have those meanings which have already been indicated above in connection with the description of the compounds of the formula (I), or (IV), according to the invention as being preferred, or particularly preferred, for $R^3$ and Z.

Process (c) according to the invention is preferably carried out using diluents. Suitable diluents for this purpose are the same organic solvents which have been mentioned above in connection with the description of process (a) according to the invention.

If appropriate, process (c) is carried out in the presence of an acid acceptor. Suitable acid-binding agents for this purpose are the same which have been mentioned above in connection with the description of process (b) according to the invention.

When carrying out process (c) according to the invention, the reaction temperatures can be varied within a substantial range. In general, the process is carried out at temperatures between 0° C. and 100° C., preferably at temperatures between 10° C. and 60° C.

Process (c) according to the invention is generally carried out under atmospheric pressure. However, it is also possible to carry out the process under increased or reduced pressure.

For carrying out process (c) according to the invention, the specifically required starting substances are generally employed in approximately equimolar amounts. However, it is also possible to use one of the two specifically employed components in a substantial excess. The reactions are generally carried out in a suitable diluent in the presence of an acid acceptor, and the reaction mixture is stirred for several hours at the specifically required temperature. Working-up in process (c) according to the invention is carried out in each case by customary methods.

To convert the compounds of the formula (I) to salts, they are stirred with suitable salt formers, such as, for example, sodium hydroxide, sodium methylate, sodium ethylate, potassium hydroxide, potassium methylate or potassium ethylate, ammonia, isopropylamine, dibutylamine or triethylamine, in suitable diluents, such as, for example, water, methanol or ethanol. The salts can then be isolated as crystalline products, if necessary after concentration.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in ornamental lawns, sports fields and grazing land, and for the selective combating of weeds in annual cultures.

The compounds of the formula (I) according to the invention are particularly suitable for selectively combating monocotyledon and dicotyledon weeds in monocotyledon crops, using the pre-emergence or the post-emergence method. They are markedly more effective than, for example, isocarbamid.

To a certain extent, the compounds according to the invention also have a fungicidal action, for example against powdery mildew on vines and against Pyricularia oryzae on rice.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foamforming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-triazin-5(4H)-one (METRIBU-ZIN) for combating weeds in soy beans; furthermore also 2,4-dichlorophenoxyacetic acid (2,4-D); 4-(2,4-dichlorophenoxy)-butyric acid (2,4-DB); 2,4-dichloro-phenoxypropionic acid (2,4-DP); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N{[(4-methoxy-6-methyl-1,3,5-triazin-2-yl)-amino]carbonyl}-benzenesulphonamide (CHLORSULFURON); N,N-di-methyl-N'-(3-chloro-4-methylphenyl)-urea (CHLORTOLURON); 4-amino-6-t-butyl-3-ethylthio-1,2,4-triazin-5(4H)-one (ETHIOZIN); [(4-amino-3,5-dichloro-6-fluoro-2-pyridinyl)oxy]-acetic acid or its 1-methylheptyl ester (FLUROXYPYR); methyl 2-[4,5-dihydro-4-methyl-4-(1-methylethyl)-5-oxo-1H-imidazol-2-yl]-4(5)-methyl-benzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-{[[((4-methoxy-6-methyl-1,3,5-triazin-2-yl)-amino)-carbonyl]-amino]-sulphonyl}-benzoic acid or its methyl ester (METSULFURON); N-(1-ethylpropyl)-3,4-dimethyl-2,6-dinitroaniline (PENDIMETHALIN); 0-(6-chloro-3-phenyl-pyridazin-4-yl) S-octyl thiocarbonate (PYRIDATE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON) and S-(2,3,3-trichloroallyl) N,N-diisopropylthiocarbamate (TRILALLATE). Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLES

EXAMPLE 1

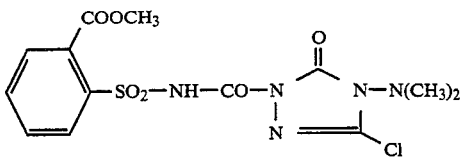

2.8 g (17.2 mmol) of 5-chloro-4-dimethylamino-2,4-dihydro-3H-1,2,4-triazol-3-one are dissolved in 60 ml of acetonitrile and 6.6 g (27.4 mmol) of 2-methoxycarbonyl-phenylsulphonyl isocyanate, dissolved in 20 ml of acetonitrile, are added to this solution with stirring. The reaction mixture is stirred for 6 hours at 20° C. and then concentrated. The residue which remains is stirred with diethyl ether, and the product obtained in crystalline form is isolated by filtration with suction.

6.9 g (99 % of theory) of 5-chloro-4-dimethylamino-2-(2-methoxycarbonyl-phenylsulphonyl-aminocarbonyl)-2,4-dihydro-3H-1,2,4-triazol-3-one of melting point 146° C. are obtained.

EXAMPLE 2

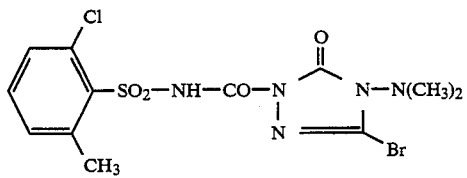

1.9 g (12.5 mmol) of 1,8-diazabicyclo-[5.4.0]-undec-7-ene (DBU) and 2.6 g (12.6 mmol) of 2-chloro-6-methyl-benzenesulphonamide are added to a solution of 4.0 g (12.2 mmol) of 5-bromo-4-dimethylamino-2-phenoxycarbonyl-2,4-dihydro-3H-1,2,4-triazol-3-one in 60 ml of acetonitrile. The reaction mixture is stirred for 3 hours at 20° C., then poured into approximately twice the volume of ice-water and then brought to a pH of approximately 2 by adding 2N hydrochloric acid. The mixture is subsequently extracted using methylene chloride, and the organic phase is washed with water, dried with sodium sulphate and filtered. The filtrate is concentrated, the residue is stirred with diethyl ether, and the product which is obtained in crystalline form is isolated by filtration with suction.

1.0 g (19% of theory) of 5-bromo-4-dimethylamino-2-(2-chloro-6-methyl-phenylsulphonyl-aminocarbonyl)-2,4-dihydro-3H-1,2,4-triazol-3-one of melting point 163° C. is obtained.

Other examples of the compounds which can be prepared analogously to Examples 1 and 2 and following the general description of the preparation processes according to the invention are those which are listed in Table 3 below.

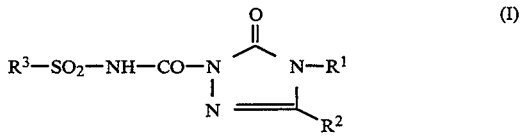

TABLE 3

Preparation examples of the compounds of the formula (I)

| Ex. No. | R¹ | R² | R³ | Melting point (°C.) |
|---|---|---|---|---|
| 3 | $CH_3$ | Cl | 2-($COOCH_3$)phenyl | 170 |
| 4 | $CH_3$ | Br | 2-($COOCH_3$)phenyl | 173 |
| 5 | $N(CH_3)_2$ | Br | 2-($COOCH_3$)phenyl | 139 |
| 6 | cyclopropyl | Br | 2-($COOCH_3$)phenyl | 155 |
| 7 | cyclopropyl | Cl | 2-($COOCH_3$)phenyl | 148 |
| 8 | $C_3H_7$ | Br | 2-($COOCH_3$)phenyl | 120 |
| 9 | $C_3H_7$ | Cl | 2-($COOCH_3$)phenyl | 119 |
| 10 | $CH_3$ | Cl | 2-Cl-3-$CH_3$-phenyl | 141 |
| 11 | $CH_3$ | Br | 2-Cl-3-$CH_3$-phenyl | 159 |
| 12 | cyclopropyl | Br | 2-Cl-3-$CH_3$-phenyl | 168 |
| 13 | cyclopropyl | Cl | 2-Cl-3-$CH_3$-phenyl | 162 |
| 14 | $C_2H_5$ | Br | 2-($COOCH_3$)phenyl | 147 |
| 15 | $C_2H_5$ | Cl | 2-($COOCH_3$)phenyl | 161 |
| 16 | $C_2H_5$ | Br | 2-Cl-3-$CH_3$-phenyl | 161 |
| 17 | $C_2H_5$ | Cl | 2-Cl-3-$CH_3$-phenyl | 156 |
| 18 | cyclopropyl | Cl | 2-($OCF_3$)phenyl | 142 |
| 19 | cyclopropyl | Br | 2-($OCF_3$)phenyl | 134 |
| 20 | $CH_3$ | Cl | 2-($OCF_3$)phenyl | 144 |
| 21 | $CH_3$ | Br | 2-($OCF_3$)phenyl | 169 |
| 22 | $C_2H_5$ | Cl | 2-($OCF_3$)phenyl | 122 |

TABLE 3-continued

Preparation examples of the compounds of the formula (I)

| Ex. No. | R¹ | R² | R³ | Melting point (°C.) |
|---|---|---|---|---|
| 23 | C₂H₅ | Br | 2-OCF₃-C₆H₄ | 133 |
| 24 | cyclopropyl | Cl | 3-methyl-2-(COOCH₃)-thiophene | 174 |
| 25 | cyclopropyl | Cl | 2-CH₃-C₆H₄ | 143 |
| 26 | cyclopropyl | Cl | 2-Br-C₆H₄ | 140 |
| 27 | cyclopropyl | Cl | 2-CF₃-C₆H₄ | 160 |
| 28 | CH₃ | Cl | 2-Br-C₆H₄ | 170 |
| 29 | cyclopropyl | Cl | 2-COOC₂H₅-C₆H₄ | 158 |
| 30 | CH₃ | Br | 2-Br-C₆H₄ | 184 |
| 31 | cyclopropyl | Br | 2-Br-C₆H₄ | 143 |
| 32 | CH₃ | Cl | 2-CH₃-C₆H₄ | 148 |
| 33 | CH₃ | Br | 2-CH₃-C₆H₄ | 143 |
| 34 | cyclopropyl | Br | 2-CH₃-C₆H₄ | 120 |
| 35 | cyclopropyl | Cl | 2-COOCH₃-C₆H₄ | 70 |
| 36 | C(CH₃)₃ | Br | 2-COOCH₃-C₆H₄ | 165 |
| 37 | cyclopropyl | Cl | 2-OCHF₂-C₆H₄ | 145 |
| 38 | cyclopropyl | Cl | 2-COOC₃H₇n-C₆H₄ | 146 |
| 39 | CH₃ | Br | 2-OCHF₂-C₆H₄ | 160 |
| 40 | cyclopropyl | Br | 2-OCHF₂-C₆H₄ | 140 |
| 41 | CH₃ | Cl | 2-OCHF₂-C₆H₄ | 133 |
| 42 | CH₃ | Br | 2-CF₃-C₆H₄ | 195 |
| 43 | OCH₃ | Br | 2-COOCH₃-C₆H₄ | |
| 44 | OCH₃ | Cl | 2-COOCH₃-C₆H₄ | |

TABLE 3-continued

Preparation examples of the compounds of the formula (I)

| Ex. No. | R¹ | R² | R³ | Melting point (°C.) |
|---|---|---|---|---|
| 45 | OC$_2$H$_5$ | Br | 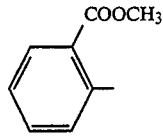 (COOCH$_3$) | |
| 46 | OC$_2$H$_5$ | Cl | 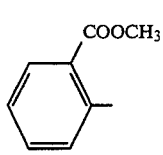 (COOCH$_3$) | |
| 47 | OC$_3$H$_7$n | Br | 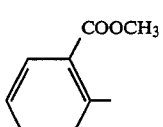 (COOCH$_3$) | |
| 48 | OC$_3$H$_7$n | Cl | 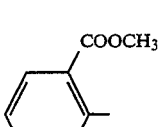 (COOCH$_3$) | |
| 49 | OCH$_3$ | Br | 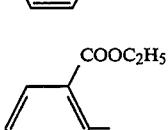 (COOC$_2$H$_5$) | |
| 50 | OC$_2$H$_5$ | Cl | 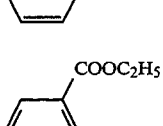 (COOC$_2$H$_5$) | |
| 51 | OC$_2$H$_5$ | Br | 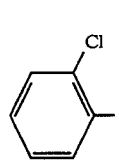 (Cl) | |
| 52 | OC$_2$H$_5$ | Cl | 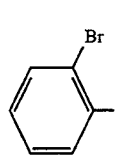 (Br) | |
| 53 | OC$_2$H$_5$ | Cl | 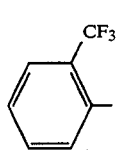 (CF$_3$) | |
| 54 | OC$_2$H$_5$ | Br | 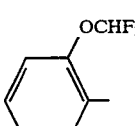 (OCHF$_2$) | |
| 55 | OC$_2$H$_5$ | Cl | 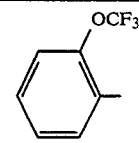 (OCF$_3$) | |
| 56 | OC$_2$H$_5$ | Cl | 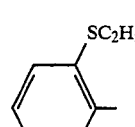 (SC$_2$H$_5$) | |
| 57 | OC$_2$H$_5$ | Cl | 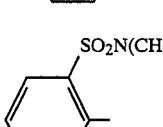 (SO$_2$N(CH$_3$)$_2$) | |
| 58 | OCH$_3$ | Cl | 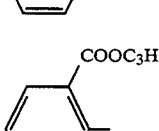 (COOC$_3$H$_7$n) | |
| 59 | OCH$_3$ | Br | 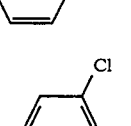 (Cl, CH$_3$) | |
| 60 | 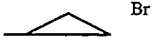 | Br | 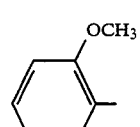 (OCH$_3$, OCH$_3$) | 145 |
| 61 | CH$_3$ | Cl | 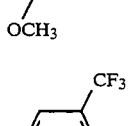 (CF$_3$) | 163 |
| 62 |  | Br | 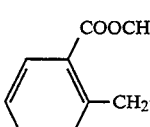 (COOCH$_3$, —CH$_2$—) | 144 |
| 63 |  | Br | 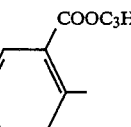 (COOC$_3$H$_7$-n) | 127 |
| 64 | 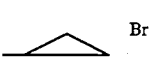 | Br | 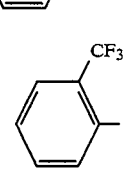 (CF$_3$) | 149 |

TABLE 3-continued

Preparation examples of the compounds of the formula (I)

| Ex. No. | R¹ | R² | R³ | Melting point (°C.) |
|---|---|---|---|---|
| 65 | CH₃ | Br | 2-SCH₃-C₆H₄ | 178 |
| 66 | CH₃ | Br | 2-SC₂H₅-C₆H₄ | 167 |
| 67 | CH₃ | Br | 2-OCH₃-4-OCH₃-C₆H₃ | 146 |
| 68 | cyclopropyl | Br | 2-SC₂H₅-C₆H₄ | 128 |
| 69 | CH₃ | Cl | 2-SCH₃-C₆H₄ | 166 |
| 70 | CH₃ | Cl | 2-SC₂H₅-C₆H₄ | 156 |
| 71 | CH₃ | Cl | 2-OCH₃-4-OCH₃-C₆H₃ | 140 |
| 72 | cyclopropyl | Cl | 2-OCH₃-4-OCH₃-C₆H₃ | 135 |
| 73 | cyclopropyl | Cl | 2-SCH₃-C₆H₄ | 158 |
| 74 | cyclopropyl | Cl | 2-SC₂H₅-C₆H₄ | 134 |
| 75 | CH₃ | Br | 2-OCH₃-C₆H₄ | 181 |
| 76 | cyclopropyl | Br | 2-OCH₃-C₆H₄ | 165 |
| 77 | cyclopropyl | Br | 2-OC₂H₅-C₆H₄ | 171 |
| 78 | CH₃ | Br | 2-OC₂H₅-C₆H₄ | 169 |
| 79 | cyclopropyl | Br | 2-COOC₂H₅-C₆H₄ | 135 |

Starting substances of the formula (II):
Example (II-1)

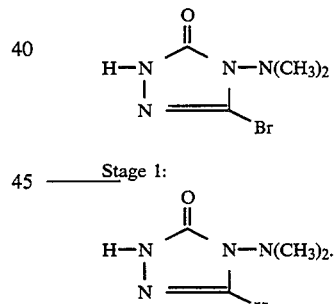

Stage 1:

856 g (4.0 mol) of diphenyl carbonate are dissolved in 588 g of ethylene chloride. With water-cooling, 245 g (4.0 mol) of dimethylhydrazine (98 %) are added dropwise, the mixture is then warmed slowly, and, after 4 hours, stirring is continued at 60° C.

After the mixture has cooled to 20° C., 200 g (4.0 mol) of hydrazine hydrate are added dropwise and stirring is continued for 12 hours. The mixture is warmed to 70°-80° C., and, after approximately 1 hour, stirred again. When cold, the solution is distilled in vacuo, during which process ethylene chloride and water are removed (bottom temperature in the end 100° C.). The above phenolic dimethyl carbodihydrazide solution is added dropwise in the course of 90 minutes at reflux temperature (approximately 102° C.) to 424 g (4.0 mol) of trimethyl orthoformate. After the methanol which has formed has been removed by distillation, phenol is distilled off in vacuo, and at a head temperature of 85°–105° C., 282 g of product mixture are subsequently obtained. This mixture is boiled with 600 ml of acetone and, after filtration at boiling temperature, the filtrate is cooled. The product which is obtained during this process in crystalline form is isolated by filtration with suction.

71 g ( 14 % of theory) of 4-dimethylamino-2,4-dihydro-3H-1,2,4-triazol-3-one of melting point 127° C. are obtained.

Stage 2:

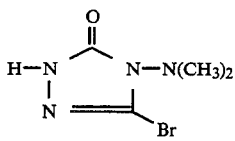

18.8 g (0.117 mol) of bromine are added with ice-cooling in the course of 2 hours to a stirred mixture of 15.0 g (0.117 mol) of 4-dimethylamino-2,4-dihydro-3H-1,2,4-triazol-3-one, 4.7 g (0.117 mol) of sodium hydroxide and 150 ml of water. The product which is obtained in crystalline form is subsequently isolated by filtration with suction.

19.6 g (81% of theory) of 5-bromo-4-dimethylamino-2,4-dihydro-3H-1,2,4-triazol-3-one of melting 163° C. are obtained.

Example (II-2)

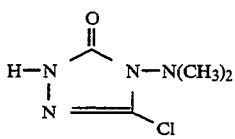

A mixture of 6.0 g (0,029 mol) of 5-bromo-4-dimethylamino-2,4-dihydro-3H-1,2,4-triazol-3-one and 200 ml of concentrated hydrochloric acid is refluxed for 3 hours. The mixture is then concentrated, the residue is taken up in a little water, the mixture is rendered neutral using sodium hydrogen carbonate, and the product which is obtained in crystalline form is isolated by filtration with suction. The filtrate is extracted using ethyl acetate, the crystalline product which has previously been isolated is added to the organic phase, and the latter is dried with sodium sulphate and filtered. The filtrate is concentrated, the residue is triturated with diethyl ether, and the product which is obtained in crystalline form during this process is isolated by filtration with suction.

3.1 g (66 % of theory) of 5-chloro-4-dimethylamino-2,4-dihydro-3H-1,2,4-triazol-3-one of melting point 158° C. are obtained.

Other examples of compounds of the formula (II) which can be prepared analogously to Examples (II-1) and (II-2) are those listed in Table 4 below.

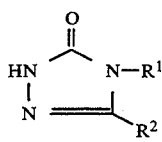

(II)

TABLE 4

Preparation examples of the compounds of the formula (II)

| Example No. | R¹ | R² | Melting point (°C.) |
|---|---|---|---|
| II-3 | ◁ | Br | 137 |
| II-4 | C₃H₇ | Br | 98 |
| II-5 | ◁ | Cl | 121 |
| II-6 | C₃H₇ | Cl | 91 |
| II-7 | C₂H₅ | Br | 142 |
| II-8 | C₂H₅ | Cl | 112 |
| II-9 | CH₂—◁ | Br | |
| II-10 | CH₂—◁ | Cl | |

Starting substances of the formula (IV):
Example (IV-1)

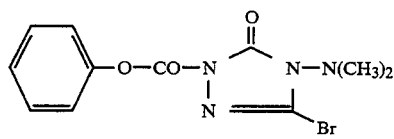

7.0 g (33.8mmol) of 5-bromo-4-dimethylamino-2,4-dihydro-3H-1,2,4-triazol-3-one are taken up in 100 ml of water and 100 ml of methylene chloride, and 0.2 g of tetrabutylammonium bromide and 1.5 g (37.5 mmol) of sodium hydroxide are added. 5.9 g (37.7 mmol) of phenyl chloroformate are then added dropwise at 20° C. with vigorous stirring, and the reaction mixture is stirred for a further 12 hours at 20° C. The organic phase is separated off, washed with water, dried with sodium sulphate and filtered. The filtrate is concentrated, the residue is stirred with diethyl ether, and the product which is obtained in crystalline form in this process is isolated by filtration with suction.

8.7 g (79 % of theory.) of 5-bromo-4-dimethylamino-2-phenoxycarbonyl-2,4-dihydro-3H1,2,4-triazol-3-one of melting point 136° C. are obtained.

USE EXAMPLES

In the following Use Examples, the known herbicide isocarbamid of formula (A) below is used as comparison substance:

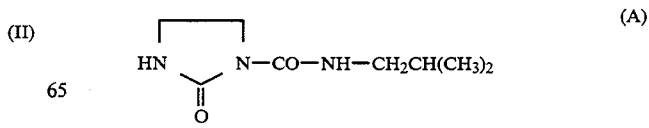

(A)

(disclosed in BE 737,449; DE 1,795,117).

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example the compounds of Preparation Examples 3, 6, 7, 29, 30, 31, 34, 64 and 79 show a clearly superior activity compared with the prior art.

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example the compounds of Preparation Examples 3, 6, 7, 12, 13, 25, 26, 28, 29, 31, 34, 37, 64 and 79 show a clearly superior activity compared with the prior art.

It is understood that the specification and examples are illustrative but not limitative of the present invention and that other embodiments within the spirit and scope of the invention will suggest themselves to those skilled in the art.

We claim:

1. A halogenated triazolinone of the formula

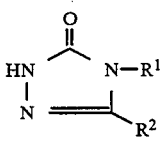

(II)

in which
R$^1$ is C$_3$–C$_6$-cycloalkyl, C$_1$–C$_6$-alkoxy or di-(C$_1$–C$_4$-alkyl)-amino, and
R$^2$ is fluorine, chlorine or bromine.

2. A halogenated triazolinone according to claim 1 wherein
R$^1$ is C$_3$–C$_6$-cycloalkyl, C$_1$–C$_4$-alkoxy or di-(C$_1$–C$_3$-alkyl)-amino, and
R$^2$ is chlorine or bromine.

3. A halogenated triazolinone according to claim 1 wherein such compound is 5-bromo-4-cyclopropyl-2,4-dihydro-3H-1,2,4-triazol-3-one of the formula

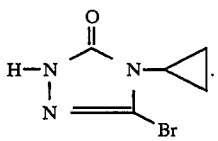

4. A halogenated triazolinone according to claim 1 wherein such compound is 5-chloro-4-cyclopropyl-2,4-dihydro-3H-1,2,4-triazol-3-one of the formula

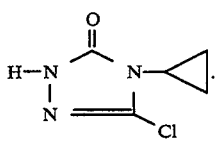

5. A halogenated triazolinone according to claim 1 wherein such compound is 5-bromo-4-dimethylamino-2,4-dihydro-3H-1,2,4-triazol-3-one of the formula

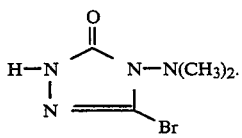

6. A halogenated triazolinone according to claim 1 wherein such compound is 5-chloro-4-dimethylamino-2,4-dihydro-3H-1,2,4-triazol-3-one of the formula

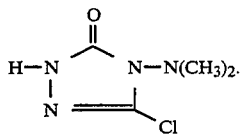

* * * * *